(12) United States Patent
Boese et al.

(10) Patent No.: US 8,050,483 B2
(45) Date of Patent: Nov. 1, 2011

(54) METHOD FOR IMAGE REGISTRATION PROCESSES AND X-RAY ANGIOGRAPHY SYSTEM

(75) Inventors: Jan Boese, Eckental (DE); Jörn Justiz, Bern (CH); Andreas Meyer, Möhrendorf (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 923 days.

(21) Appl. No.: 12/070,484

(22) Filed: Feb. 19, 2008

(65) Prior Publication Data

US 2008/0212858 A1 Sep. 4, 2008

(30) Foreign Application Priority Data

Mar. 2, 2007 (DE) .......................... 10 2007 010 806

(51) Int. Cl.
*G06K 9/00* (2006.01)
(52) U.S. Cl. ........................ 382/132; 382/154
(58) Field of Classification Search .................. 382/100, 382/151, 276
See application file for complete search history.

(56) References Cited

U.S. PATENT DOCUMENTS

| | | | | |
|---|---|---|---|---|
| 5,710,875 A * | 1/1998 | Harashima et al. | ........... | 345/419 |
| 6,661,913 B1 * | 12/2003 | Zhang et al. | .................. | 382/154 |
| 7,013,040 B2 * | 3/2006 | Shiratani | ....................... | 382/154 |
| 7,852,977 B2 * | 12/2010 | Wegener et al. | .................. | 378/4 |
| 2002/0075456 A1 * | 6/2002 | Shiratani | ......................... | 353/31 |
| 2003/0021381 A1 * | 1/2003 | Koppe et al. | .................. | 378/163 |
| 2003/0194050 A1 * | 10/2003 | Eberhard et al. | ................ | 378/37 |
| 2004/0127796 A1 * | 7/2004 | Chalana et al. | ................ | 600/449 |
| 2004/0249303 A1 * | 12/2004 | Serra | .............................. | 600/545 |
| 2005/0004454 A1 * | 1/2005 | Mitschke et al. | ............. | 600/427 |
| 2006/0244746 A1 * | 11/2006 | England et al. | .................. | 345/419 |
| 2007/0167801 A1 * | 7/2007 | Webler et al. | ................. | 600/459 |

FOREIGN PATENT DOCUMENTS

| | | |
|---|---|---|
| DE | 10322738 A1 | 12/2004 |
| DE | 10357184 A1 | 7/2005 |
| EP | 1 640 972 A1 | 3/2006 |

OTHER PUBLICATIONS

Graeme Patrick Penney, "Registration of Tomographic Images to X-ray Projections for Use in Image Guided Interventions", University of London, Dec. 1999, pp. 36-58 and 97-159.
Jörn Anemüller, Michael Kleinschmidt and Birger Kollmeier, "Blinde Quellentrennung als Vorverarbeitung zur robusten Spracherkennung", Deutsche Gesellschaft für Akustik e. V. (DEGA), Fortschritte der Akustik—DAGA 2000, Oldenburg, pp. 1-2.
Joseph V. Hajnal, Derek L. G. Hill and David J. Hawkes, "Medical Image Registration" CRC Press, 2001, pp. 1-70.
Siemens Medical Solutions, "syngo iPilot—Effective guidance during interventional procedures", Nov. 2005, pp. 1-2.

* cited by examiner

*Primary Examiner* — Jingge Wu
*Assistant Examiner* — Avinash J Yentrapati

(57) ABSTRACT

Registration of preoperatively acquired MRI images of soft parts to intraoperatively acquired X-ray images of soft parts is not possible. The invention shows a way of nevertheless using such preoperatively acquired images for superimposition with 2D projections of the soft parts, taking an indirect route via 3D/3D registration of images of the spinal column. For this purpose, 3D image data sets of the spinal column must be obtained separately on the one hand using MRI and on the other using the X-ray imaging system so that the 3D/3D registration produces a mapping rule which then also applies to the preoperatively acquired images of the soft part if the soft part images and the spinal images are acquired without intervening change in the patient position in the MRI scanner.

8 Claims, 1 Drawing Sheet

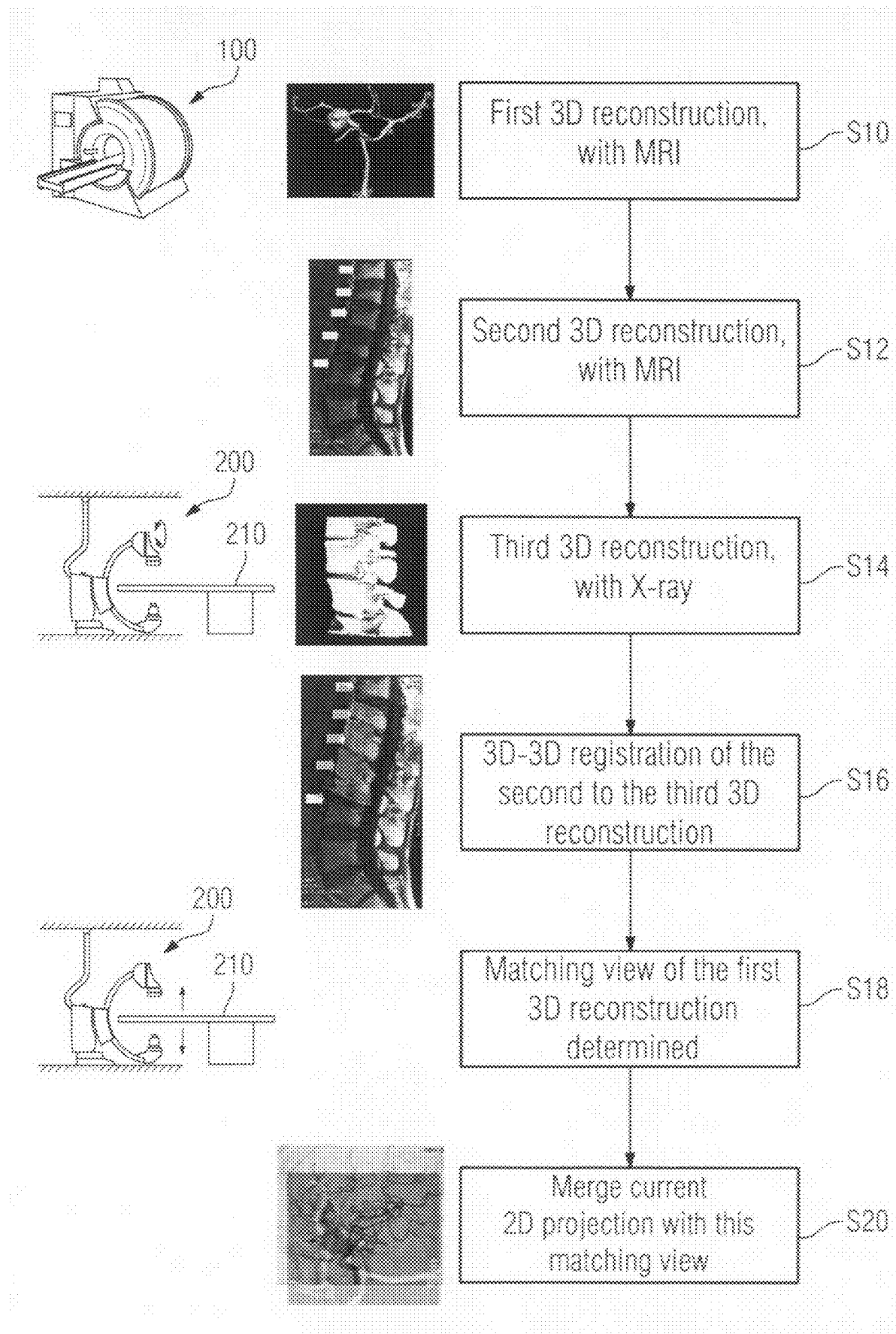

METHOD FOR IMAGE REGISTRATION PROCESSES AND X-RAY ANGIOGRAPHY SYSTEM

CROSS REFERENCE TO RELATED APPLICATIONS

This application claims priority of German application No. 10 2007 010 806.2 filed Mar. 2, 2007, which is incorporated by reference herein in its entirety.

FIELD OF THE INVENTION

The invention relates to a method for creating extended possibilities for using patient image data that is unsuitable for the application of registration processes, and an X-ray angiography system for use in conjunction with the inventive method.

BACKGROUND OF THE INVENTION

These are registration processes which create extensive imaging possibilities to assist a treating doctor during a medical intervention or surgical procedure. Image data sets are regularly acquired preoperatively using image acquisition systems which show the image area of interest in an optimum manner. During an operation, additional images are then acquired which in themselves do not necessarily provide sufficient information. The previously acquired image data is now registered to the image data acquired during the operation. The term registration means that a rule for mapping between the coordinate system of the first image data set and the coordinate system of the second image data set is determined. The two different image acquisition systems used for generating the two image data sets can only be related to one another if the patient is in a fixed basic position in each case because of the image information. For positionally and dimensionally correct mapping of the coordinate systems to one another, image recognition is often used in order to be able to recognize structures in the image data. The registration of two 3D image data sets to one another is generally known. An overview of this may be found in, for example, the book by J. V. Hajnal, D. L. G. Hill, D. J. Hawkes "Medical Image Registration", CRC Press, 2001. The image acquisition systems used to generate the individual 3D image data sets may be different. Thus, for example, the registration of a 3D image data set acquired using an MRI scanner to a 3D rotation angiography image data set is known. Also, 2D/3D registration, i.e. the registration of a 3D image data set to 2D images is known, see e.g. the dissertation by P. Penney, "Registration of Tomographic Images to X-ray Projections for Use in Image Guided Interventions", University of London, 1999, pages 36 to 58 and pages 97 to 159.

To use image recognition for registration it is necessary for the image structures in the image data to be recognizable. Often, however, the areas of interest in the patient are soft parts. A classical example of this is a patient's heart. Although soft parts can be well imaged by MRI, they are difficult to recognize on X-ray images. Registration between preoperatively and intraoperatively acquired cardiac image data is therefore ruled out if the intraoperatively acquired image data is obtained using an X-ray image acquisition system. It is helpful if, along with the image data relating to the soft parts, bones such as the spinal column, for example, are imaged. In the case of MRI, however, the image volume which can be acquired within typical acquisition times of 20 seconds is too small: heart and spinal column cannot be visualized simultaneously in one image. Extending the acquisition time is possible only with difficulty, as the patient has to hold his breath during the scan. Moreover, the imaging of muscle tissue such as cardiac muscle tissue requires the use of specific image acquisition parameters for MRI and the imaging of bones the use of quite different image acquisition parameters. If an image is to contain both bone and muscle tissue, a compromise would have to made, leading to unsatisfactory results.

After a mapping rule has been determined by the registration process, the preoperatively acquired image data and the intraoperatively acquired image data are merged into one visualization. In Siemens Medical, this can be effected by the syngo iPilot system. Details concerning syngo iPilot are described e.g. in the two-page leaflet "syngo iPilot—Effective guidance during interventional procedures" dated November 2005 which is available from Siemens Medical Solutions.

It would be desirable if the high-quality image data for soft parts which can be acquired by MRI (and also e.g. using 3D ultrasound imaging systems) could be used in some way to assist the treating doctor, which necessitates correlation with intraoperatively acquired image data.

SUMMARY OF THE INVENTION

The object of the invention is therefore to extend the possibilities for using patient data that is unsuitable for (directly) employing registration processes.

This object is achieved by a method and an X-ray angiography system having the features as claimed in the claims.

The inventive method thus comprises the following steps:
receiving of a first image acquisition parameter set by an image acquisition system and (possibly in response to a start input) execution of image acquisition steps by the first image acquisition system to obtain a first 3D image data set,
receiving of a second image acquisition parameter set by the first image acquisition system and (possibly in response to a start input) execution of image acquisition steps by the first image acquisition system to obtain a second 3D image data set,
transmission of the first and the second 3D image data set from the first image acquisition system to a second image acquisition system,
receiving of image acquisition instructions and execution of image acquisition steps by the second image acquisition system to obtain a third 3D image data set,
determining a mapping rule for coordinate transformation from the second 3D image data set to the third 3D image data set,
using the mapping rule to obtain at least one visualization based on the first 3D image data set.

The above described problem that in the case of MRI, for example, soft parts and vertebrae cannot be imaged simultaneously is solved by acquiring two different 3D image data sets, e.g. the first 3D image data set as a representation of the heart using an image acquisition parameter set suitable for cardiac imaging and the second 3D image data set as a representation of the spinal column using an image acquisition parameter set suitable for spinal imaging. The prerequisite is that the patient does not move between acquisition of the first and the second 3D image data set in the first image acquisition system. The coordinate system is then the same for the first and the second image data set. The third 3D image data set can then contain a representation of the vertebrae matching the second 3D image data set so that registration (determining the mapping rule) is easily possible. As the first and the second 3D image data set have the same coordinate system, this mapping rule can also be used between the first 3D image data set and representations belonging to the coordinate system of the second image acquisition system.

For example, the method comprises the following steps:
  receiving of image acquisition instructions and execution of image acquisition steps by the second image acquisition system to obtain at least one 2D image (typically a 2D projection image),
  overlaying of the 2D image with a representation based on the first 3D image data set.

Alternatively, for direct acquisition of such 2D images by the second image acquisition system, systems of this kind can also be used to acquire 2D image representations whose coordinate system is linked to that of the second image acquisition system. For example, a 2D image could also be provided by an electromagnetic localization system permanently connected to the second image acquisition system.

The invention to a certain extent involves taking an indirect route from the heart (first 3D image data set) via imaging of the vertebrae (second 3D image data set), via a second imaging of the vertebrae (third 3D image data set) to further images of the heart. With the aid of the imagings of the vertebrae, a mapping rule is determined which, in the subsequent process, links the cardiac imaging (first 3D image data set) to the further cardiac imagings (2D images).

It should be noted that although the same coordinate system must apply to the first and the second 3D image data set and therefore, during their acquisition, the patient must not change position, the patient's position can be changed in a defined manner when the patient is in the second image acquisition system. For example, it may be necessary to move the patient positioning table. A change of the patient's position is then part of the image acquisition steps for obtaining a 2D image in the second image acquisition system, and this position change is then easily factored in when obtaining the representation based on the 3D image data set, and superimposition is then therefore also possible.

As reiterated many times above, a feature of the preferred embodiments of the invention is that the first image acquisition system is an MRI scanner or alternatively comprises a 3D ultrasound image acquisition system, and that the second image acquisition system is an X-ray angiography system.

The object of the invention is also achieved by an X-ray angiography system designed to carry out the method. The X-ray angiography system accordingly comprises:
  means for receiving a first and a second 3D image data set from an external image acquisition system and means for storing the 3D image data sets,
  means for obtaining a 3D X-ray image data set as a third 3D image data set and means for storing the third 3D image data set,
  means for determining a mapping rule for coordinate transformation of the second 3D image data set to the third 3D image data set, and
  means for applying the mapping to the first image data set.

The X-ray angiography system is preferably designed, in per se known manner, to acquire 2D X-ray image projections and comprises means for overlaying representations based on the first image data set with the 2D projection images using the mapping rule.

Unlike in the standard case, the X-ray angiography system must now therefore manage (receive and store) two 3D image data sets from an external image acquisition system and be suitably designed, e.g. suitably programmed in a microprocessor belonging to the X-ray angiography system, to perform registration to one of the 3D image data sets and to use the mapping rule obtained during registration for the other of the 3D image data sets.

BRIEF DESCRIPTION OF THE DRAWINGS

A preferred embodiment of the invention will now be described with reference to the accompanying drawing which constitutes a flowchart representing the steps of an embodiment of the inventive method and, in relation to the steps, schematically illustrates the relevant image acquisition system as well as images obtained using said image acquisition system.

DETAILED DESCRIPTION OF THE INVENTION

In a patient's body there is an area of interest to the treating doctor which in the present case shall be located in a soft part. For example, the doctor is interested in the left atrium of the heart in order to prepare an atrial ablation. An MRI scanner 100 is optimally suited for visualizing such soft parts. In step S10 of the method according to the invention, a sequence of 2D slices of the area of interest is accordingly acquired preoperatively, the image acquisition parameters being optimally selected for imaging the area of interest and there being obtained in known manner from the sequence of 2D slices a 3D reconstruction which, in the present case, constitutes a first 3D image data set. Directly thereafter, with the patient's position in the MRI scanner 100 remaining unchanged, a sequence of 2D slices of vertebral bodies is acquired, this time the image acquisition parameters creating optimum conditions for good visualization of vertebral bodies, and there being generated in known manner from the 2D slices a 3D reconstruction which in the present case constitutes a second 3D image data set. The steps S10 and S12 can also take place in reverse order, it being merely essential that the coordinate system of the first 3D reconstruction is the same as the coordinate system of the second 3D reconstruction.

The actual operation is now carried out. The patient is positioned in a C-arm X-ray system 200 (which functions as an X-ray angiography system) on a patient table 210. In step S14 rotation angiography is performed in a known manner in order to image at least some of the vertebral bodies that were imaged in step S12. This provides a third 3D reconstruction.

In step S16, a 3D/3D registration of the two reconstructions of the spinal column is performed to determine a mapping rule between the coordinate system of the patient in the MRI scanner 100 and the coordinate system of the patient on the positioning table 210 in the X-ray angiography system 200.

In step S18, a matching view is now determined from the first 3D reconstruction using the mapping rule, it being assumed here that the coordinate system of the first 3D reconstruction is the same as that of the second 3D reconstruction so that the mapping rule determined in step S16 also maps the first 3D reconstruction to the coordinate system of the X-ray angiography system 200. The matching view is determined such that it matches a projection (a 2D image) which the C-arm has acquired at a currently given angle, at a currently given magnification and possibly subject to other permanently set variables. For determining the matching view, in addition to the mapping rule, a possible displacement of the patient positioning table 210 can also be factored in as well as the position of the X-ray C-arm. The matching view which was determined in step S18 is then superimposed on the 2D X-ray projection acquired at the predefined position of the C-arm. A precise superimposition fit (merging) is possible e.g. using the Siemens Medical syngo iPilot system.

On the indirect route via imaging of the vertebral bodies (steps S12, S14), 3D registration (step S16) is made possible which produces a mapping rule which can be used for soft part image data which is itself totally unsuitable for the use of registration methods. The invention therefore enables steps S18 and S20 to be carried out, allowing images acquired preoperatively using an MRI scanner 100 to be merged with images taken intraoperatively using the X-ray angiography system.

The core element of the invention is determining the mapping rule. After carrying out step S16 relating thereto, further possibilities emerge. The mapping rule links the first 3D reconstruction to the coordinate system of the X-ray angiography system. Other systems linked to this coordinate system can then be set in relation to the first 3D reconstruction. For example, there can be linked to the X-ray angiography system 200 an electromagnetic localization system which can be used to produce images which can likewise be superimposed on matching views obtained from the first 3D reconstruction.

The invention claimed is:

1. A method for an image registration process, comprising:
    creating a first 3D image data set of a patient by a first image acquisition system, wherein the first 3D image data set comprises imaging of a part of the body of the patient comprising soft tissue, wherein one or more imaging parameters of the first image acquisition system are selected for soft tissue imaging;
    creating a second 3D image data set of the patient by the first image acquisition system, wherein the second 3D image data set comprises imaging of a part of the body of the patient comprising an skeletal structure, wherein one or more imaging parameters of the first image acquisition system are selected for skeletal imaging;
    transmitting the first and the second 3D image data set of the patient to a second image acquisition system, which is not suitable for soft tissue imaging;
    creating a third 3D image data set of the patient by the second image acquisition system, wherein the third 3D image data set comprises imaging of the part of the body of the patient comprising the skeletal structure imaged by the first image acquisition system;
    determining a mapping rule for a coordinate transformation from the second 3D image data set to the third 3D image data set based on a registering of the skeletal structure having been respectively imaged by the first image acquisition system in the second 3D image data set and by the second image acquisition system in the third 3D image data set;
    processing the determined mapping rule to relate the first 3D image data set which comprises imaging of the part of the body of the patient comprising soft tissue, to a coordinate system of the second image acquisition system, which is not suitable for soft tissue imaging; and
    generating a representation of the part of the body of the patient comprising soft tissue from the first 3D image data set related to the coordinate system of the second image acquisition system, and effective for registering the representation of the part of the body of the patient comprising soft tissue with a 2D image recorded by second image acquisition system.

2. The method as claimed in claim 1, wherein the representation of the patient from the first 3D image data set comprises a position change of the patient which is captured by the 2D image.

3. The method as claimed in claim 1, wherein the first image acquisition system comprises an MRI scanner.

4. The method as claimed in claim 1, wherein the first image acquisition system comprises a 3D ultrasound image acquisition system.

5. The method as claimed in claim 1, wherein the second image acquisition system comprises an X-ray angiography system.

6. An X-ray angiography system, comprising:
    an input that receives a first and a second 3D image data set of a patient from an external image acquisition system, wherein the first 3D image data set comprises imaging of a part of the body of the patient comprising soft tissue, wherein one or more imaging parameters of the first image acquisition are selected for soft tissue imaging and further wherein the second 3D image data set comprises imaging of a part of the body of the patient comprising an skeletal structure, wherein one or more imaging parameters of the first image acquisition system are selected for skeletal imaging;
    an X-ray acquisition device that creates a 3D X-ray image data set of the patient as a third 3D image data set, wherein the third 3D image data set comprises imaging of the part of the body of the patient comprising the skeletal structure imaged by the first image acquisition system;
    a memory that stores the first, the second, and the third 3D image data set; and
    an image processing device that determines a mapping rule for a coordinate transformation from the second 3D image data set to the third 3D image data set based on a registering of the skeletal structure having been respectively imaged by the first image acquisition system in the second 3D image data set and by the second image acquisition system in the third 3D image data set, and applies the mapping rule to the first image data set to generate a representation of the part of the body of the patient comprising soft tissue from the first 3D image data set related to the coordinate system of the second image acquisition system, and effective for registering the representation of the part of the body of the patient comprising soft tissue with a 2D image recorded by second image acquisition system.

7. The method as claimed in claim 1, wherein the part of the body of the patient comprising soft tissue comprises a heart of the patient and the part of the body of the patient comprising the skeletal structure comprises a vertebral structure of the patient.

8. The X-ray angiography system as claimed in claim 6, wherein the part of the body of the patient comprising soft tissue comprises a heart of the patient and the part of the body of the patient comprising the skeletal structure comprises a vertebral structure of the patient.

* * * * *